United States Patent [19]

Meyer

[11] Patent Number: 4,904,794
[45] Date of Patent: Feb. 27, 1990

[54] PYRAZOLINE COMPOUNDS

[75] Inventor: Hans R. Meyer, Binningen, Switzerland

[73] Assignee: Ciba-Geigy Corporation, Ardsley, N.Y.

[21] Appl. No.: 159,981

[22] Filed: Feb. 24, 1988

[51] Int. Cl.$^4$ ............................................ C07D 231/06
[52] U.S. Cl. .................................. 548/377; 548/375; 548/379; 8/573
[58] Field of Search ...................... 548/379, 377, 375; 8/573

[30] Foreign Application Priority Data

Mar. 5, 1987 [CH] Switzerland ............... 812/87

[56] References Cited

U.S. PATENT DOCUMENTS

| | | | |
|---|---|---|---|
| 3,255,203 | 6/1966 | Schinzel et al. | 548/379 |
| 3,378,389 | 4/1968 | Schellhammer et al. | 548/379 |
| 3,574,195 | 4/1971 | Hajek | 260/239.9 |
| 3,619,234 | 11/1971 | Weihsbach | 117/33.5 T |
| 3,639,419 | 2/1972 | Rosenberger et al. | 548/379 |
| 3,865,816 | 2/1975 | Mengler | 260/239.9 |
| 3,939,154 | 2/1976 | Bolton et al. | 548/379 |
| 3,957,815 | 5/1976 | Mengler | 260/310 D |
| 3,998,346 | 10/1976 | Schmid | 548/379 |
| 3,998,812 | 12/1976 | Mengler et al. | 548/379 |
| 4,045,169 | 8/1977 | Mengler | 8/1 W |

FOREIGN PATENT DOCUMENTS

| | | | |
|---|---|---|---|
| 2516053 | 1/1976 | Fed. Rep. of Germany . | |
| 2641814 | 3/1978 | Fed. Rep. of Germany . | |
| 1095010 | 5/1955 | Switzerland | 548/379 |

Primary Examiner—Mary C. Lee
Assistant Examiner—Catherine S. Kilby Scalzo
Attorney, Agent, or Firm—Edward McC. Roberts

[57] ABSTRACT

New pyrazoline compounds of the formula

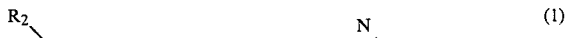

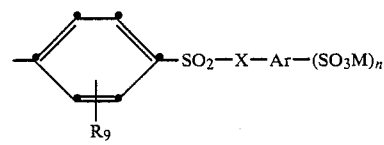

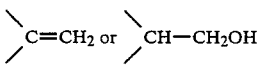

in which
X is 1,4-phenylene, $$\diagdown C=CH_2 \text{ or } \diagdown CH-CH_2OH$$

if n is 1 or if $R_7$ or $R_8$ contains an $SO_3M$ radical, also a methylene or $-CH_2CH(OH)-CH_2O-$ group or an unbranched $C_1-C_4$ alkyleneoxy group, a direct bond or oxygen, $R_1$, $R_2$ and $R_3$ independently of one another are hydrogen, chlorine or $C_1-C_4$ alkyl, $R_7$ is $C_1-C_4$ alkyl, chlorophenyl, hydrogen, phenyl or $-C_6H_4-SO_3M$, $R_8$ is H, $C_1-C_4$ alkyl, $-CH_2SO_3M$, carboxyl, $C_2-C_5$ carboalkoxy, carbamoyl or carboxymethyl, $R_9$ is H, chlorine or $C_1-C_4$ alkyl, Ar is a phenyl radical which is unsubstituted or substituted by non-chromophores or, if X is a direct bond, also a naphthalene radical, M is hydrogen or one equivalent of a non-chromophoric cation and m and n are the number nought or 1, which can be used as fluorescent brighteners for synthetic and natural fibres, especially for polyamide.

A process for the preparation of these compounds, their use as fluorescent brighteners and agents containing the compounds for the fluorescent brightening of fibres and lacquers composed of acetylcellulose, wool and especially polyamide, and also novel hydrazines as an intermediate in the preparation of the compounds.

6 Claims, No Drawings

PYRAZOLINE COMPOUNDS

The invention relates to pyrazoline compounds of the formula

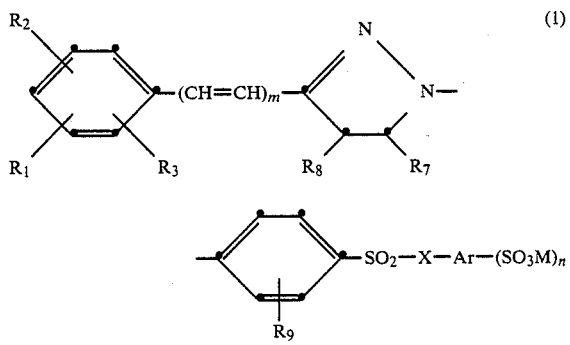
(1)

in which
X is 1,4-phenylene,

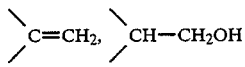

or, if n is 1 or if $R_7$ or $R_8$ contains an $SO_3M$ radical, also a methylene or —$CH_2CH(OH)$—$CH_2O$—group or an unbranched $C_1$-$C_4$alkyleneoxy group, a direct bond or oxygen, $R_1$, $R_2$ and $R_3$ independently of one another are hydrogen, chlorine or $C_1$-$C_4$alkyl, $R_7$ is $C_1$-$C_4$alkyl, chlorophenyl and, in particular, hydrogen, phenyl or —$C_6H_4$—$SO_3M$, $R_8$ is carboxyl, $C_2$-$C_5$carboalkoxy, carbamoyl, carboxymethyl and, in particular, H, $C_1$-$C_4$alkyl or —$CH_2SO_3M$, $R_9$ is $C_1$-$C_4$alkyl or, in particular, hydrogen, methyl or chlorine, Ar is a phenyl radical which is unsubstituted or substituted by a non-chromophore or, if X is a direct bond, also a naphthalene radical, M is hydrogen or one equivalent of a non-chromophoric cation and m and n are the number nought or 1, which can be used as fluorescent brighteners for synthetic and natural fibres, in particular for polyamide.

Alkyl is to be understood as meaning both linear and branched carbon radicals. The alkyleneoxy group is attached to the sulfonyl group by means of a terminal C atom. The following may be mentioned as examples of non-chromophoric substituents: phenylalkyl, fluorine, alkoxy, alkyl, benzyloxy, phenyl, cycloalkyl, alkenyl, alkenyloxy, alkylsulfonyl, phenylsulfonyl, benzylsulfonyl, carboxyl, carboalkoxy, acyloxy, carbamoyl, sulfamoyl, cyano, acylmaino and, in particular, $C_1$-$C_4$alkyl, $C_1$-$C_4$alkoxy, phenoxy and chlorine. The compounds of the formula (1) preferably contain not more than one sulfo group, i.e., if, for example, $R_7$ is a sulfophenyl group or $R_8$ is a sulfomethyl group, n is 0. Two adjacent alkyl groups can also form a tetralyl or indanyl ring. M in formula (1) is, for example, an alkaline earth metal, such as magnesium or calcium, but is preferably hydrogen, an alkali metal, such as lithium, sodium, potassium and unsubstituted or substituted ammonium, such as ammonium, monoethanolammonium, diethanolammonium, triethanolammonium, monoisopropanolammonium, diisopropanolammonium, triisopropanolammonium, triethhlammonium or tetraethylammonium.

Compounds in which n is 1 are preferred. Compared with the representatives free from sulfo groups, those containing sulfo groups have the advantage of solubility in water. Particularly high whitening effects are shown by compounds in which X is a direct bond.

Preferred compounds of the formula (1) are those of the formula

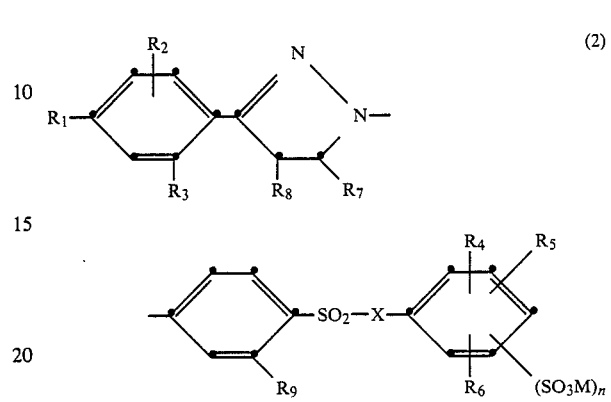
(2)

in which
X is 1,4-phenylene,

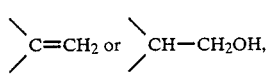

or, if n is 1 and/or if $R_8$ contains the radical —$SO_3M$, also a linear $C_1$-$C_4$alkyleneoxy group, oxygen or, preferably, a direct bond, $R_1$ to $R_3$ are H, Cl or methyl, $R_4$ and $R_5$ are H, Cl, $C_1$-$C_4$alkyl, $C_1$-$C_4$alkoxy or phenoxy or together are the members required to form tetralin or indane ring, $R_6$ is H or methyl, $R_7$ is H or phenyl, $R_8$ is H, $C_1$-$C_4$alkyl or —$CH_2SO_3M$, $R_9$ is H or Cl, and n and M are as defined in formula 1.

The invention relates particularly to pyrazoline compounds of the formula

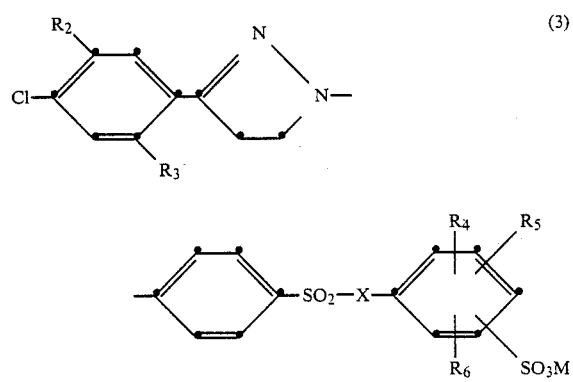
(3)

in which
X is the methylene group, a linear $C_1$-$C_4$alkylenoxy group or, preferably, a direct bond, $R_2$ and $R_3$ are hydrogen, chlorine or methyl, $R_4$ and $R_5$ are hydrogen, chlorine, $C_1$-$C_4$alkyl or methoxy or together are the members required to form a tetraline ring, and $R_6$ and M are as defined in formula 2, and, in particular, to pyrazoline compounds of the formula

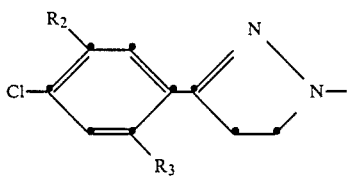

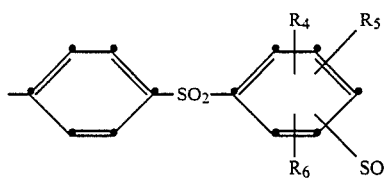

in which
R₂ is hydrogen or, in particular, chlorine, R₃ is hydrogen or, in particular, methhyl, R₄ is hydrogen or C₁-C₄alkyl, R₅ and R₆ are hydrogen or methyl and M is as defined in formula 2.

The invention also embraces mixtures of the compounds claimed here. Any desired shades of whitening effects can be produced by combining suitable reddish-tinged representatives with greenish-tinged representatives.

1-Phenylpyrazoline compounds having sulfoalkylsulfonyl substituents in the p-position relative to the phenyl radical are already known from German Patents 1,419,329, 1,670,988, 1,719,355, 2,011,552, 2,142,564, 2,516,053, 2,524,927 and 2,641,814, and sulfoarylsulfonamides are already known from German Patent 2,403,308. Compared with these types, the pyazoline compounds according to the invention are distinguished, in particular, by better whitening effects.

The preparation of the pyrazoline compounds according to the invention is effected by a process in which a compound of the formula

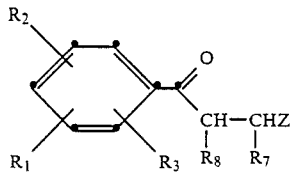

or

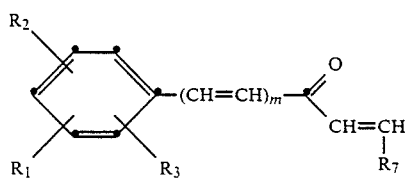

in which the Zs are leaving groups, such as halogen, a di-C₁-C₄alkylamino group or a morpholino, pyrrolidino or piperidino radical is reacted in a manner known per se with hydrazines of the formula

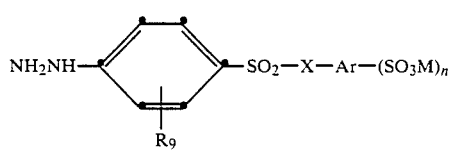

The reaction is advantageously carried out in an aqueous, aqueousorganic or organic medium, at temperatures of 50°-120° C. The mixing ratio in this reaction is preferably maintained at a figure such that the educts are still adequately dissolved and the products are precipitated. Examples of suitable organic solvents are alcohols, such as methanol, ethanol, isopropanol, n-propanol, sec-butanol, n-butanol and ethylene glycol monomethyl ether, and also dimethylformamide or acetic acid.

In a further process, pyrazolinesulfonic acids of the formula

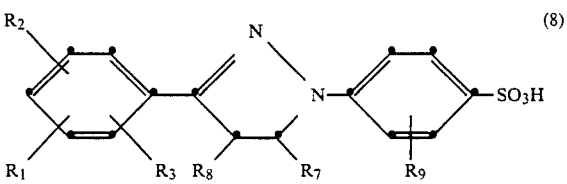

or salts thereof are converted in a known manner via the sulfochloride (German Auslegeschrift 1,695,103) into the sulfinic acids or salts thereof, and the latter are subjected to a condensation reaction with compounds of the formula $$Z—X—Ar—(SO_3M)_n \quad (9)$$

in which Z is halogen, in suitable cases (where n is nought) with postsulfonation. This process is particularly suitable for pyrazolines of the formula 1 in which m and n are nought and X is a substituted or unsubstituted methylene group.

The hydrazines of the formula 7 in which n is nought are in part known or can be prepared by a known process (German Patent 1,285,886, J. pr. Chem., 132 (1931) pages 34–36, Chem. Abs. 53 (1959) 8122i).

The hydrazines of the formula 7 in which n is 1 are novel and constitute a further subject of the invention. They are obtained by diazotizing anilines of the formula

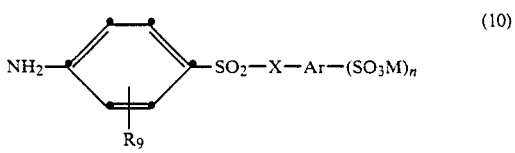

in a manner known per se and reducing the diazonium compounds. The reduction is advantageously effected by means of sulfite in a neutral to a slightly alkaline medium, after which the reaction product is subsequently treated with acid.

The anilines of the formula 10 in which X is a direct bond are obtained, for example, from p-nitrochlorobenzenes and benzensulfinic acids in accordance with European Patent 101,664. The sulfonation of the p-nitrophenyl sulfones formed as intermediates is effected, for example, by means of oleum, SO₃, sulfuric acid or chlorosulfonic acid, if appropriate with subsequent saponification of the sulfochloride formed. Reaction with oleum at 0° to 100° C. is preferred.

In another process, in which X is CH₂ [Helv. Chim. Acta 66 (1983) 1046–1053], a p-acetaminobenzenesulfinic acid is reacted with benzyl halides, and the resulting sulfones are saponified and, if desired, sulfonated, as previously described, or, advantageously, first sulfonated and then saponified (British Patent 2,006,252). In a 3rd process p-acetaminobenezenesulfochloride is subjected to a condensation reaction in the presence of Friedel-Crafts catalysts with suitable aromatic compounds to give the corresponding sulfones [Gazz. chim. ital. 79 (1949) 621–9], which are then reacted further as described previously. Conversely, sulfones are also obtained by subjecting acetanilide to a condensation reaction with substituted benzenesulfochlorides in the presence of aluminium chloride (Swiss Patent 278,939).

In a further method, known per se, hydrazines of the formula 7 in which n is 1 are obtained, similarly to the unsulfonated representatives, by reacting the sulfones of the formula (11)

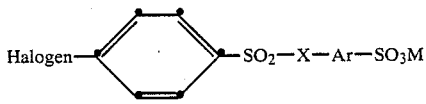

in which halogen is Cl, Br or I, with hydrazine. Excess hydrazine hydrate at 90° C.–125° C., for example, is used in this reaction; if necessary, for example if (11) is sparingly soluble, a suitable solvent, such as ethylene glycol monomethylether, is added.

The sulfones of the formula 11 are obtained, for example, by a Friedel-Crafts reaction between chlorobenzene and arylsulfonyl chlorides (DRP 701,954; J. Applied Chem. USSR 50 (1977) 1532–5) or conversely between p-chlorophenylsulfonyl chloride and suitable aromatic compounds (German Offenlegungsschrift 2,038,167; Chem. Ber. 109 (1976) 2315–26). The sulfonation of the resulting p-chlorophenyl sulfones is then effected as in the case of the p-nitrophenyl sulfones, for example by means of oleum (see Example 2, Method d).

The compounds according to the invention are suitable for brightening various substrates. The representatives which are insoluble in water exhibit good properties when brightening fibres and lacquers composed of polyamide, acetylcellulose and wool. The anionic compounds are particularly suitable for brightening polyamide and wool applied to the textiles. The polyamide fibres are also brightened by treatment in a scouring bath.

It is also possible to employ mixtures of these fluorescent brighteners, such as are produced, for example, in the course of synthesis.

EXAMPLE 1

A warm solution of 7.9 g of 3,3',4'-trichloro-6'-methylpropiophenone in 25 ml of n-propanol is added dropwise at 70° C. to a solution of 9.0 g of the hydrazine of the formula

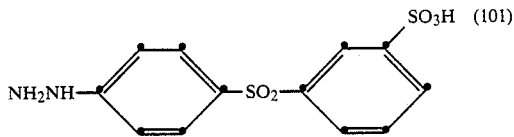

(content 91%) in 25 ml of n-propanol and 25 ml of water. The pH is kept at 2–3 by the gradual addition of 30% sodium hydroxide solution. The solution is stirred for a further hour at 70° C. and then overnight at reflux temperature. It is then neutralized to pH 8 and allowed to cool. The product which has been precipitated is filtered off with suction, washed with 2% sodium chloride solution and with n-propanol and dried in vacuo at 100° C. This gives 6.0 g of the compound of the formula

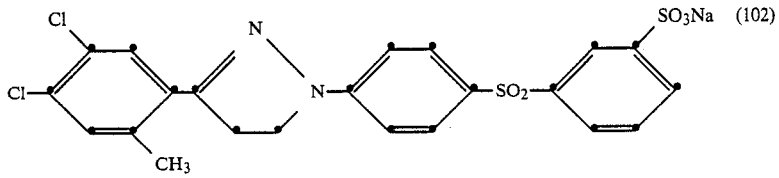

which is recrystallized from 70% aqueous n-propanol.

The hydrazine of the formula 101 used as the starting material can be prepared as follows:

235 g of the compound of the formula

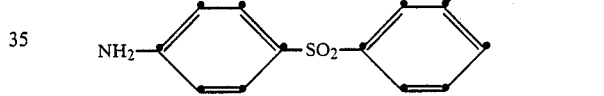

are dissolved in 940 ml of hot water. 110.8 g of concentrated hydrochloric acid are added with vigorous stirring, the mixture is cooled and a solution of 52.5 g of sodium nitrite in 75 ml of water is added dropwise at 5°–10° C. Stirring is continued for an hour at the same temperature, a correction is made, if necessary, with sulfamic acid or sodium nitrite to a starch/potassium iodide end point, and the diazonium solution is added dropwise, with stirring and at room temperature, in the course of about 20 minutes to 585.3 g of an aqueous 40% solution of sodium bisulfite, the pH of which has previously been adjusted to 7 with 30% sodium hydroxide solution (approx. 150 ml). After the expiry of 1 hour, the resulting solution is heated to 60° C. and 443.4 g of concentrated hydrochloric acid are carefully added dropwise, so that the evolution of sulfur dioxide can be kept under control. After being stirred for a further hour at reflux temperature, the mixture is cooled to 5° C. and the precipitated product is filtered off with suction, washed with methanol and water and dried in vacuo at 80° C. This gives 241.5 g of a colourless powder.

EXAMPLE 2

The hydrazines of the general formula 104 are obtained in accordance with Example 1 in the form of free sulfonic acids, and the pyrazolines of the general formula 105 are obtained therefrom in the form of their sodium salts (Table I) by condensation with the appropriate 62-chloropropiophenones. The hydrazines of the formula 104 containing sulfo groups can often be prepared better by reverse diazotization, i.e. by adding an aqueous solution of the alkali metal salt of the parent sulfonic acid and sodium nitrite to aqueous hydrochloric acid. The solvent used for the conversion of the hydrazines is a 20:3 mixture of n-propanol and water. Unless specifically mentioned, the substituents $R_8$ and $R_9$ are hydrogen.

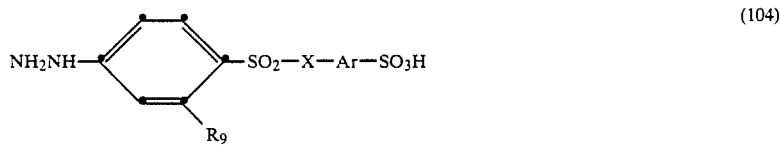

(104)

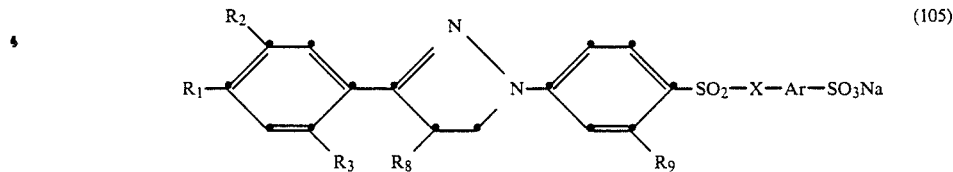

(105)

TABLE I

| (105) R₁ | R₂ | R₃ | (104) or (105) —X—Ar—SO₃H(Na) | (104) recrystallized from | Method of preparation | (105) Formula |
|---|---|---|---|---|---|---|
| Cl | H | H | ⟨benzene⟩-SO₃H(Na) | H₂O | (a) | (106) |
| Cl | Cl | H | " |  |  | (107) |
| Cl | H | H | ⟨benzene⟩-CH₃, SO₃H(Na) | n-Propanol —H₂O 1:1 | (a) | (108) |
| Cl | Cl | H | " |  |  | (109) |
| Cl | H | Cl | " |  |  | (110) |
| Cl | Cl | CH₃ | " |  |  | (111) |
| H | H | H | " |  |  | (112) |
| Cl | H | H | —CH₂—⟨benzene⟩—SO₃H(Na) | — | (b) (c) | (113) |
| Cl | Cl | H | " |  |  | (114) |
| Cl | Cl | CH₃ | " |  |  | (115) |
| Cl | H | H | ⟨benzene⟩-Cl, SO₃H(Na) | n-Propanol —H₂O 1:1 | (a) | (116) |
| Cl | Cl | H | " |  |  | (117) |
| Cl | Cl | CH₃ | " |  |  | (118) |
| Cl | H | H | ⟨naphthalene⟩-SO₃H(Na) | — | (a) | (119) |

TABLE I-continued

| (105) R₁ R₂ R₃ | (104) or (105) —X—Ar—SO₃H(Na) | (104) recrystallized from | Method of preparation | (105) Formula |
|---|---|---|---|---|
| Cl Cl CH₃ | biphenyl-SO₃H(Na) | n-Propanol—H₂O 1:1 | (c) | (120) |
| Cl H H | 2,5-dimethylphenyl-SO₃H(Na) | n-Propanol—H₂O 1:1 | (b) (d) | (121) |
| Cl Cl H | " | | | (122) |
| Cl Cl CH₃ | " | | | (123) |
| Cl H H | 2,3-dimethyl-6-SO₃H(Na)-phenyl (CH₃ at 2,3; SO₃H at 6) | n-Propanol—H₂O 1:1 | (b) | (124) |
| Cl Cl H | " | | | (125) |
| Cl Cl CH₃ | " | | | (126) |
| Cl H H | 4-CH₃**-phenyl-SO₃H(Na) | | (a) | (127) |
| Cl H H | phenyl*** -SO₃H(Na) | — | (a) | (128) |
| Cl H H | 2,3-dimethyl-5-SO₃H(Na)-phenyl | n-Propanol—H₂O 1:1 | (a) | (129) |
| Cl Cl H | " | | | (130) |
| Cl Cl CH₃ | " | | | (131) |
| Cl H H | 2,3-dimethyl-5-SO₃H(Na)-phenyl (isomer) | n-Propanol—H₂O 1:1 | (a) | (132) |
| Cl Cl H | " | | | (133) |
| Cl Cl CH₃ | " | | | (134) |

TABLE I-continued

| (105) R₁ R₂ R₃ | (104) or (105) —X—Ar—SO₃H(Na) | (104) recrystallized from | Method of preparation | (105) Formula |
|---|---|---|---|---|
| Cl H H | 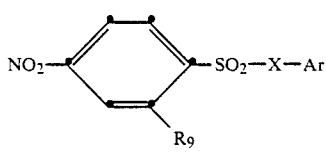 SO₃H(Na) | — | (a) | (135) |
| Cl Cl H | " | | | (136) |
| Cl Cl CH₃ | " | | | (137) |
| Cl H H | H₃O SO₃H(Na) OCH₃ | MC*—H₂O 1:1 | (c) | (138) |
| Cl Cl H | " | | | (139) |
| Cl Cl CH₃ | " | | | (140) |
| Cl H H | —(CH₂)₃—O— SO₃H(Na) | MC*—H₂O 1:1 | (d) | (141) |
| Cl Cl H | " | | | (142) |
| Cl Cl CH₃ | " | | | (143) |
| Cl Cl CH₃ | C₂H₅ SO₃H(Na) | n-Propanol —H₂O 1:1 | (d) | (144) |
| Cl Cl CH₃ | OH \| —CH₂CHCH₂O— SO₃H(Na) | H₂O | (d) | (145) |

*MC = Ethyleneglycol monomethylether
**R₈ = CH₃
***R₉ = Cl

The sulfonic acids of the formula 10 required for the preparation of the hydrazines in Table I of the general formula 104 were obtained by 3 different methods:
Method a:
Sulfonating the nitro compounds of the formula (150)

NO₂—⌬—SO₂—X—Ar
         |
         R₉

With 25% oleum at 20°–60° C. (the temperature depending on the reactivity) and subsequently reducing the product with iron in dilute aqueous acetic acid by the Bechamp method in accordance with European Patent 101,664 or 102,325.
Method b:
Sulfonating the anilines of the formula

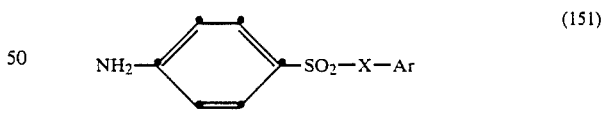

(151)

with oleum, as described previously.
Method c:
Sulfonating the acetylanilines of the formula

(152)

as under b. After the reaction mass has been discharged onto ice water it is heated at reflux temperature for 1 to 2 hours, whereupon saponification takes place. Exceptions: In order to sulfonate the compound of the formula

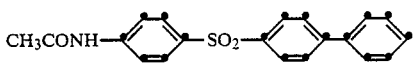 (153)

Melting point 240° C. (Acetonitrile)

it is sufficient to use concentrated sulfuric acid instead of oleum (1 hour a 60° C.). The compound is obtained by a Friedel-Crafts reaction between biphenyl and 4-acetaminobenzenesulfochloride in nitrobenzene, in the presence of aluminium chloride at 70°–100° C.

The sulfonic acids of the formula 11 required for the preparation of the hydrazines in Table I of the general formula 104 were obtained as follows:

Method d:
Chlorine compounds of the formula

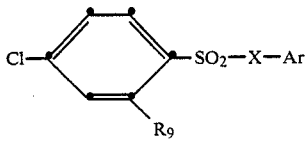 (154)

are sulfonated with oleum or sulfuric acid as described previously.

The sulfonation of the compounds of the formula

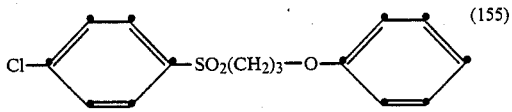 (155)

Melting point 74°–50° C., is effected by means of concentrated sulfuric acid (1 hour at room temperature). Discharging the mixture onto ice and salting up the product with sodium chloride gives the compound of the formula

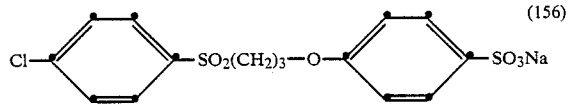 (156)

which is recrystallized from 4:1 n-propanol/water.

The compound

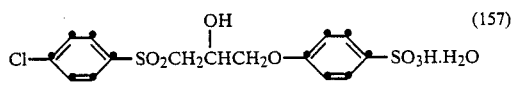 (157)

is prepared by stirring 13.1 g of the compound of the formula

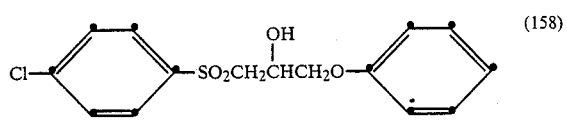 (158)

in 50 ml of concentrated sulfuric acid for 2 hours at room temperature, discharging the solution onto ice, forming a total volume of 190 ml, and heating the solution at 100° C. for 1 hour. After cooling to 0° C., the precipitated product is filtered off with suction, washed repeatedly with acetone and dried in a high vacuum.

Yield 8.4 g.

The starting material of the formula 158 is obtained by adding phenyl glycidic ether (20% excess) dropwise to a solution of sodium 4-chlorobenzenesulfonate in aqueous alcohol at 70° C. and at pH 7–8, the liberated sodium hydroxide solution being neutralized continuously with concentrated hydrochloric acid. When the reaction is complete, the resulting solution is evaporated to dryness in vacuo, the residue is stirred in methylene chloride/water, the two phases are separated in a separating funnel, the methylene chloride phase is dried and evaporated, and the residue is crystallized from ether or isopropanol, melting point 77°–8° C.

The sulfone of the formula

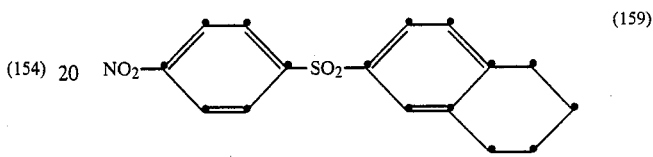 (159)

required for the preparation of the compounds of the formulae 135 to 137 is obtained as follows:

93.7 g of 1,2,3,4-tetrahydronaphthalene-6-sulfochloride are introduced in portions and with vigorous stirring at 70° C. into 114.4 g of a 40% solution of sodium bisulfite which has been diluted with 320 ml of water and adjusted to pH 7–8 with 30% sodium hydroxide solution. The pH is kept at 7–8 by the simultaneous dropwise addition of sodium hydroxide solution. Stirring is continued, with the temperature constant, until no further sodium hydroxide solution is consumed (total consumption approx. 120 ml of 30% NaOH), and the mixture is warmed for a further hour at 80° C. The solution is clarified by filtration, cooled and acidified with approx. 50 ml of concentrated hydrochloric acid with further cooling. The colourless product precipitated is filtered off with suction, washed with 120 ml of water in 3 portions and dried to constant weight over calcium chloride in a high vacuum. 78.5 g of 1,2,3,4-tetrahydronaphthalene-6-sulfinic acid are obtained (melting point 82°–5°).

21.2 g of sodium carbonate are introduced carefully and with vigorous stirring (foaming) into a suspension of 78.5 g of this sulfinic acid in 150 ml of dimethyl sulfoxide. 63.0 g of 1-chloro-4-nitrobenzene are added to the resulting solution, and the mixture is stirred at 100° C. for 4 hours. It is diluted while still warm with 150 ml of ethanol and 300 ml of water and allowed to cool. The precipitated product is filtered off with suction and washed repeatedly with water and methanol. This gives 98.8 g of the compound of the formula 159, melting point 135°–6° (from isopropanol).

EXAMPLE 3

The non-sulfonated hydrazines of the general formula 201, and from these the pyrazolines of the general formula 202 (Table 2), are obtained similarly to Example 2. The hydrazines were prepared by method e or f.

Method e:
Diazotizing and reducing the corresponding anilines

Method f:
Reacting the corresponding p-chlorophenyl sulfones with hydrazine hydrate in the presence of methylcellosolve at reflux temperature.

TABLE 2

Structure (201): NH₂NH—⟨phenyl⟩—SO₂—X—Ar

Structure (202): R₁,R₂,R₃-substituted phenyl—CH=N—N(—)—⟨phenyl⟩—SO₂—X—Ar

| (202) R₁ | R₂ | R₃ | (201) or (202) —X—Ar | (201) Method of preparation | (201) Melting point | (202) Melting point (°C.) | Formula |
|---|---|---|---|---|---|---|---|
| Cl | H | H | —⟨C₆H₃(OCH₃)⟩—⟨C₆H₄—OCH₃⟩ | (e) | | 198–208° | (203) |
| Cl | Cl | H | —⟨C₆H₄—CH₃⟩ | (e) | 151° | 208° | (204) |
| Cl | Cl₂ | CH₃ | —⟨C₆H₄—CH₃⟩ | | | 250° | (205) |
| Cl | H | H | —CH(CH₂OH)—⟨C₆H₅⟩ | (e) | 177°(dcomp.) | 166° | (206) |
| Cl | H | H | —⟨C₆H₄⟩—O—⟨C₆H₅⟩ | (f) | 191° | 205° | (207) |
| Cl | H | H | —⟨2,4-(CH₃)₂C₆H₃⟩ | (f) | ca 120° | 228° | (208) |

The 4-(2'/4'-methoxyphenylsulfonyl)-phenylhydrazine required for the preparation of the mixture of isomers of the formula 203 is obtained in a customary manner by diazotizing and reducing with sodium sulfite the mixture of isomers of the formula

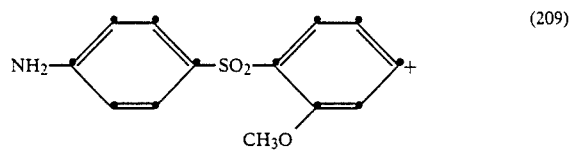

(209)

-continued

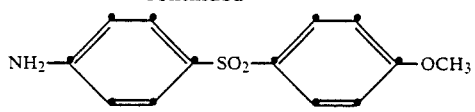

Melting point 185°–188° C. This mixture is obtained by a Friedel-Crafts reaction between 4-acetylaminobenzenesulfochloride and excess anisole in the presence of aluminium chloride at 100°–120° C., and by saponifying the reaction product with hydrochloric acid at reflux temperature. The product is isolated by separating off the organic phase, washing it with water and sodium hydroxide solution, removing, by distillation in a high vacuum, excess anisole and the phenyl sulfanilate formed as a biproduct, and crystallizing the residue from ethyl acetate.

The hydrazine required for the preparation of the compound of the formula 206 is obtained as follows:

26.4 g of phenylethylene oxide are added dropwise in the course of 1 hour, at reflux temperature and with stirring, to a solution of 39.8 g of p-acetylaminobenzene-sulfinic acid and 35.4 g of sodiumacetate trihydrate in 200 ml of ethanol. After refluxing for a further 5 hours, the mixture is allowed to cool and 300 ml of water are added. The precipitated product is filtered off with suction, washed repeatedly with water and dried in vacuo at 100° C. This gives 35.9 g of the compound of the formula

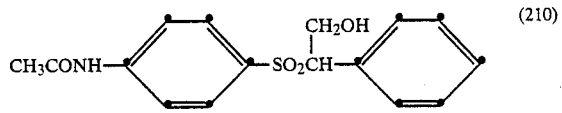
(210)

Melting point 193°–4° C. (recrystallized from acetonitrile). 31.9 g of the compound of the formula 210 are stirred for 1 hour at reflux temperature in 200 ml of water and 100 ml of concentrated hydrochloric acid. Sodium hydroxide solution is added to the resulting solution until the pH is ~12, whereupon the product is precipitated. This gives 26.5 g of the compound of the formula

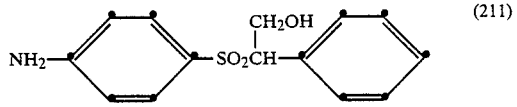
(211)

Melting point 252°–3° C. (recrystallized from ethylene-glycol monomethyl ether).

16.4 g of the compound of the formula 211 are dissolved by heating in 60 ml of water and 57 ml of concentrated hydrochloric acid. After the mixture has been cooled to 0° to 5° C., a solution of 4.1 g of sodium nitrite in 10 ml of water is added dropwise, with stirring, in the, course of 15 minutes. Stirring is continued for a further hour at the same temperature, and the resulting diazonium salt solution is added dropwise, with stirring, to 46.0 g of an aqueous 40% solution of sodium bisulfite solution, the pH of which has previously been adjusted to 7 with 30% sodium hydroxide solution. The pH is kept at 7 by the simultaneous addition of further sodium hydroxide solution. The total consumption of 30% sodium hydroxide solution is approx. 73 ml. After the expiry of 1 hour, the solution is heated to 60° C. and 34.9 g of concentrated hydrochloric acid are carefully added dropwise (evolutio of sulfur dioxide). After being stirred at reflux temperature for a further 3 hours, the solution is cooled and its pH is adjusted to 10 with sodium hydroxide solution, whereupon the desired hydrazine is precipitated as the free base. The product is filtered off with suction, washed repeatedly with water and dried in vacuo at 80° C. This gives 16.1 g of the compound of the formula

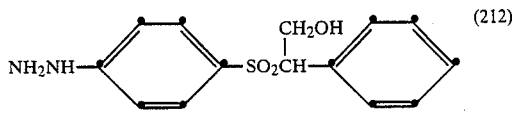
(212)

Melting point 177°–178° (decomp.). The compound can be recrystallized from ethanol.

EXAMPLE 4

11.0 g of the compound of the formula 206 are introduced, with stirring and at room temperature, into 30.0 g of concentrated sulfuric acid, and stirring is continued for 3 hours. The solution is poured into a mixture of ice and water, so that a volume of 200 ml results. After being stirred with 40 g of sodium chloride, the precipitated product is filtered off with suction under cold conditions, and stirred into 100 ml of ice water, and the pH of the suspension is adjusted to 10–11 by the dropwise addition of 30% sodium hydroxide solution. The temperature is allowed to rise to 80°, and the pH is kept constant by adding further sodium hydroxide solution (total consumption 8.5 ml). When the reaction is complete, the mixture is cooled and the precipitated product is filtered off with suction, washed repeatedly with water and then with methanol. This gives 9.6 g of the compound of the formula

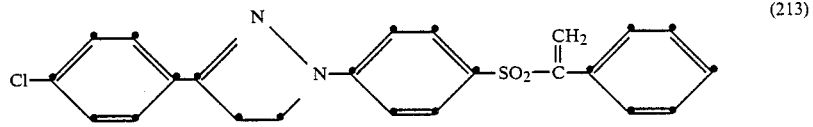
(213)

Melting point 183°–4° (from n-butanol and xylene).

EXAMPLE 5

7.3 g of benzal-4-chloroacetophenone and 10.8 g of the hydrazine of the formula 101 (91% content) are stirred into 150 ml of ethanol, 5 ml of concentrated hydrochloric acid are added, and the mixture is heated at reflux temperature for 18 hours. The resulting solution is neutralized to pH 8 with 30% sodium hydroxide solution and allowed to cool slowly. The precipitated product is filtered off with suction, washed with ethanol and dried in vacuo at 100° C. This gives 16.6 g of the compound of the formula

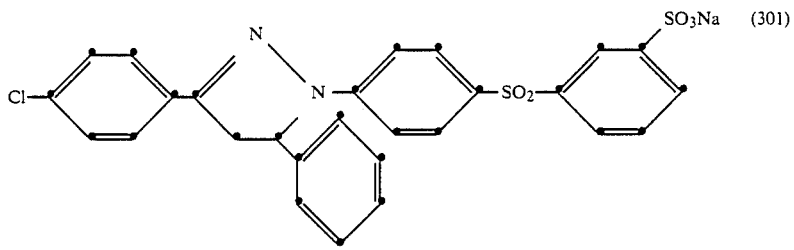
(301)

in the form of a nearly colourless powder. Purification is effected by recrystallization from a 7:3 mixture of n-propanol and water, with the aid of active charcoal.

If the equivalent amount of dibenzalacetone is used in this example instead of benzal-4-chloroacetophenone, the compound of the formula

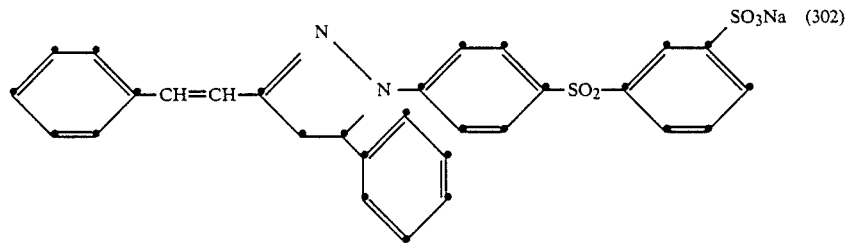
(302)

is obtained. It is recrystallized from methanol/ethanol.

EXAMPLE 6

If the internal salt of the Mannich base 3-(4''-morpholino)-2-sulfomethyl-3',4'-dichloro-6'-methylpropiophenone is subjected to a condensation reaction with the corresponding hydrazines in ethylene glycol monomethyl ether/water in the presence of sodium acetate and at reflux temperature, the compounds of the formulae

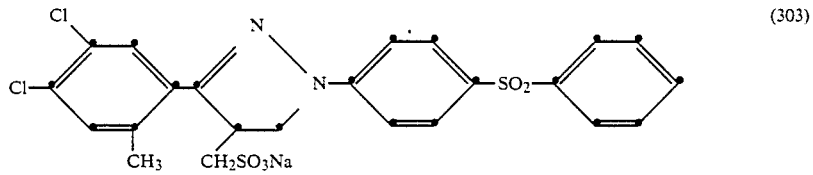
(303)

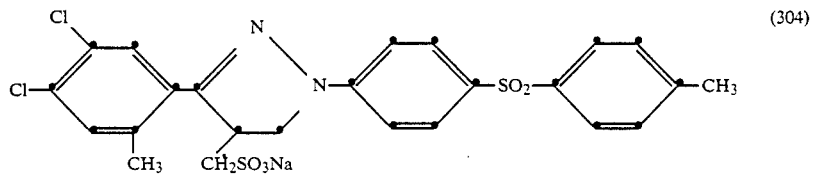
(304)

or, analogously, the compound of the formula

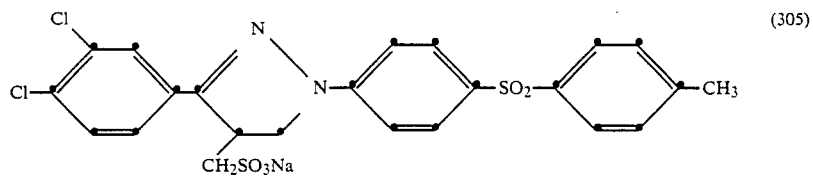
(305)

are obtained.

EXAMPLE 7

3.55 g of the compound of the formula

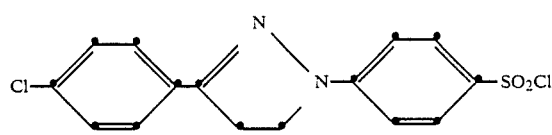
(310)

are added in portions to a solution of 4.7 g of the Na salt of p-phenolsulfonic acid in 12.5 ml of ethanol and 5.25 ml of 2N sodium hydroxide solution.

The mixture is stirred, first at room temperature and then at reflux temperature, while a little sodium hydroxide solution is simultaneously added dropwise until a constant pH of 8 has been reached. After cooling, the product is filtered off with suction, washed with alcohol and dried. It is purified by being taken up in ethyleneglycol monomethyl ether at room temperature, freeing the solution from insoluble material by filtration and evaporating it to dryness in vacuo on a rotary evaporator. Extracting the residue by boiling with alcohol and filtration with suction at room temperature gives the compound of the formula are obtained analogously.

EXAMPLE 8

The following hydrazines of the formula 104, and from them the pyrazolines of the formula 105 in which $R_8$ and $R_9$ are hydrogen, can be obtained similarly to the preceding examples: (Table 3)

(311)

The compounds of the formulae

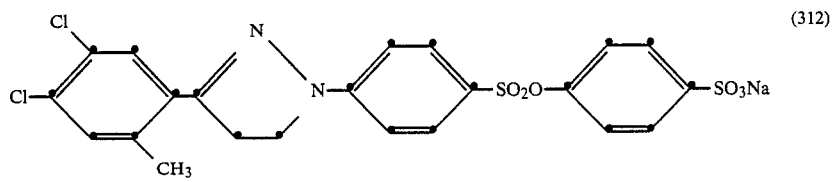
(312)

and

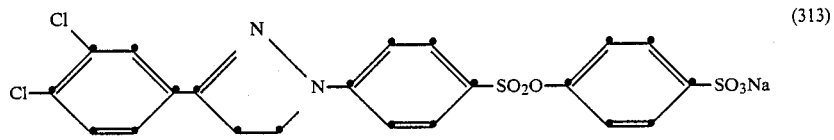
(313)

TABLE 3

| (105) | | | (104) or (105) | Formula (105) |
|---|---|---|---|---|
| $R_1$ | $R_2$ | $R_3$ | —X—Ar—SO$_3$H(Na) | |
| Cl | H | H | ![phenyl-CH(CH₃)₂ with SO₃H(Na)] | (401) |
| Cl | Cl | H | ![phenyl-CH(CH₃)₂ with SO₃H(Na)] | (402) |
| Cl | Cl | CH$_3$ | ![phenyl-CH(CH₃)₂ with SO₃H(Na)] | (403) |
| Cl | H | H | CH$_3$ / SO$_3$H(Na) / CH(CH$_3$)$_2$ on phenyl | (404) |
| Cl | Cl | H | CH$_3$ / SO$_3$H(Na) / CH(CH$_3$)$_2$ on phenyl | (405) |

TABLE 3-continued
| | (105) | | (104) or (105) | |
|---|---|---|---|---|
| $R_1$ | $R_2$ | $R_3$ | $-X-Ar-SO_3H(Na)$ | Formula (105) |
| Cl | Cl | $CH_3$ | 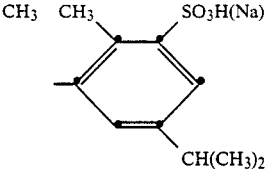 | (406) |
| Cl | H | H | 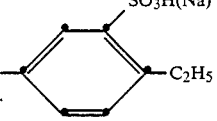 | (407) |
| Cl | Cl | H | 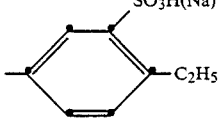 | (408) |
| Cl | H | H | 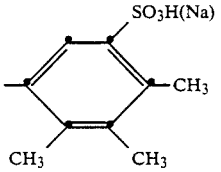 | (409) |
| Cl | Cl | H | 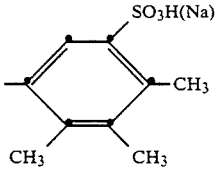 | (410) |
| Cl | Cl | $CH_3$ | 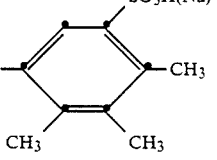 | (411) |
| Cl | H | H | 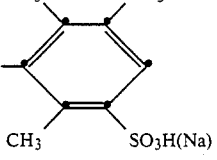 | (412) |
| Cl | Cl | H | 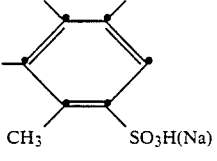 | (413) |
| Cl | Cl | $CH_3$ | 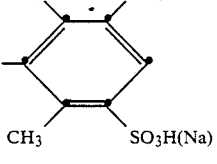 | (414) |

TABLE 3-continued
| | (105) | | (104) or (105) | |
|---|---|---|---|---|
| $R_1$ | $R_2$ | $R_3$ | —X—Ar—SO$_3$H(Na) | Formula (105) |
| Cl | H | H | 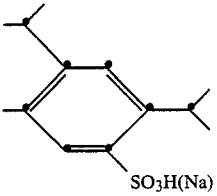 | (415) |
| Cl | Cl | H | 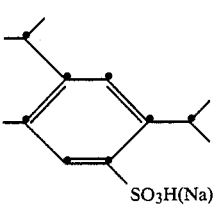 | (416) |
| Cl | Cl | CH$_3$ | 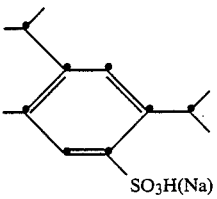 | (417) |
| Cl | H | H | 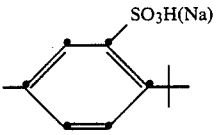 | (418) |
| Cl | Cl | H | 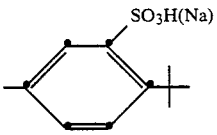 | (419) |
| Cl | Cl | CH$_3$ | 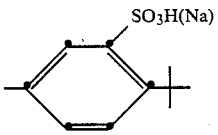 | (420) |
| Cl | H | H | 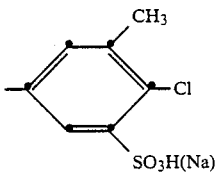 | (421) |
| Cl | Cl | H | 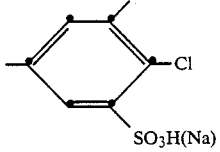 | (422) |

TABLE 3-continued
| | (105) | | (104) or (105) | |
|---|---|---|---|---|
| $R_1$ | $R_2$ | $R_3$ | —X—Ar—$SO_3H(Na)$ | Formula (105) |
| Cl | Cl | $CH_3$ | 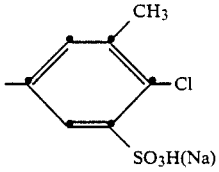 | (423) |
| Cl | H | H | 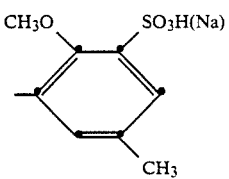 | (424) |
| Cl | Cl | H | 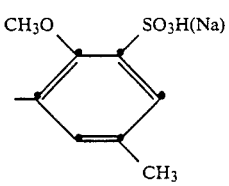 | (425) |
| Cl | Cl | $CH_3$ | 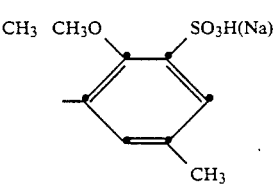 | (426) |
| Cl | H | H | 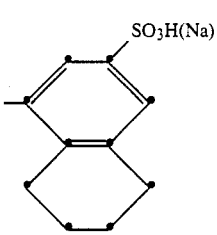 | (427) |
| Cl | Cl | $CH_3$ | 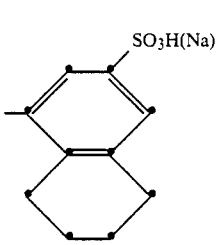 | (428) |
| Cl | H | H | 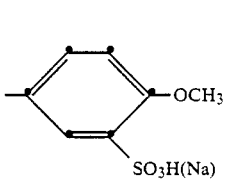 | (429) |
| Cl | Cl | H | 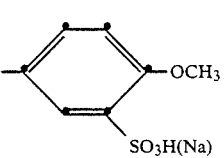 | (430) |

TABLE 3-continued

| | (105) | | (104) or (105) | |
|---|---|---|---|---|
| R₁ | R₂ | R₃ | —X—Ar—SO₃H(Na) | Formula (105) |
| Cl | Cl | CH₃ | benzene ring with —OCH₃ and SO₃H(Na) | (431) |
| Cl | H | H | indane-like bicyclic with SO₃H(Na) | (432) |
| Cl | Cl | H | indane-like bicyclic with SO₃H(Na) | (433) |
| Cl | Cl | CH₃ | indane-like bicyclic with SO₃H(Na) | (434) |
| Cl | H | H | benzene with CH₃ and SO₃H(Na) | (435) |
| Cl | Cl | H | benzene with CH₃ and SO₃H(Na) | (436) |
| Cl | Cl | CH₃ | benzene with CH₃ and SO₃H(Na) | (437) |
| Cl | H | H | benzene with CH₃ and SO₃H(Na) | (438) |
| Cl | Cl | H | benzene with CH₃ and SO₃H(Na) | (439) |

TABLE 3-continued

| R₁ | R₂ | R₃ | —X—Ar—SO₃H(Na) (104) or (105) | Formula (105) |
|----|----|----|-------------------------------|---------------|
| Cl | Cl | CH₃ | phenyl with CH₃ and SO₃H(Na) | (440) |
| Cl | H | H | biphenyl—SO₃H(Na) | (441) |
| Cl | H | H | —(CH₂)₂—O—phenyl—SO₃H(Na) | (442) |
| Cl | Cl | H | —(CH₂)₂—O—phenyl—SO₃H(Na) | (443) |
| Cl | Cl | CH₃ | —(CH₂)₂—O—phenyl—SO₃H(Na) | (444) |
| Cl | Cl | CH₃ | —CH₂—O—phenyl—SO₃H(Na) | (442) |

EXAMPLE 9

A polyamide 6,6 fabric is treated on a dyeing machine at a liquor ratio of 1:20 with an aqueous liquor containing 0.05%, relative to the weight of the fabric, of a compound of the formula 102, 109, 111, 123, 126, 131, 134 or a 1:1 mixture of 109 and 111, 3 g/l of an adduct formed from 1 mole of stearyl alcohol and 35 moles of ethyleneoxide, 3 g/l of buffered sodium dithionite and 1 ml/l of 80% acetic acid. Application is carried out in accordance with the following temperature programme: 40°–97° for 30 minutes, 100° for 30 minutes and 100°–40° for 15 minutes. The fabric is then rinsed in softened water and dried. It has a good white effect.

EXAMPLE 10

A polyamide fabric (nylon Webtricot type 6) is padded at room temperature with an aqueous liquor containing 0.5 g/l of a brightener mentioned in Example 9 and 1 g/l of an adduct formed from 1 mole of stearyl alcohol and 35 moles of ethylene oxide, 1 g/l of an adduct formed from 1 mole of p-tert-octylphenol and 8 moles of ethylene oxide, 90 ml of 95% ethanol and 5 ml/l of 80% acetic acid. The liquor pickup is 110%. The goods are then dried and thermofixed at 190° for 40 seconds. The fabric treated in this way has a good white effect.

EXAMPLE 11

Bleached woollen serge is treated on a dyeing machine at a liquor ratio of 1:25 in an aqueous liquor containing 0.05%, relative to the weight of the material, of a compound of the formula 109, 111 or 132, 3 g/l of buffered sodium dithionite and 1 ml/l of 80% acetic acid (added after 45 minutes). Application is carried out for 75 minutes at 60° C. After being rinsed in demineralized water, the fabric has a good white effect.

EXAMPLE 12

A cellulose acetic fabric is introduced, at a liquor ratio of 1:25, into an aqueous liquor containing 0.1%, relative to the weight of the fabric, of the compound of the formula 206 and 1 g/l of ethoxylated fatty alcohol. The temperature of the treatment bath is raised to 80° C. and is kept at this level for 30 minutes. After being rinsed and dried the fabric is strongly whitened.

What is claimed is:

1. A pyrazoline compound of the formula

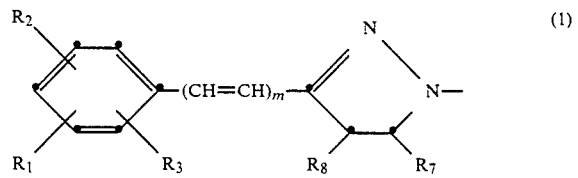

(1)

-continued

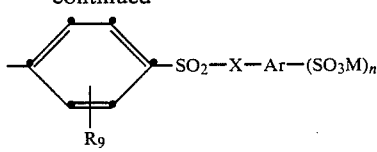

in which
X is 1,4-phenylene,

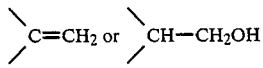

or, if n is 1 or if $R_7$ or $R_8$ contains an $SO_3M$ radical, X is also a methylene or —$CH_2CH(OH)$—$CH_2O$— group or an unbranched $C_1$-$C_4$alkyleneoxy group, a direct bond or oxygen, $R_1$, $R_2$ and $R_3$ independently of one another are hydrogen, chlorine or $C_1$-$C_4$alkyl, $R_7$ is $C_1$-$C_4$alkyl, chlorophenyl, hydrogen, phenyl or —$C_6H_4$—$SO_3M$, $R_8$ is H, $C_1$-$C_4$alkyl, —$CH_2SO_3M$, carboxyl, $C_2$-$C_5$carboalkoxy, carbamoyl or carboxymethyl, $R_9$ is H, chlorine or $C_1$-$C_4$alkyl, Ar is a phenyl radical which is unsubstituted or substituted by a nonchromophore or, if X is a direct bond, Ar is also a naphthalene radical, M is hydrogen or one equivalent of an alkali metal, an alkaline earth metal or an unsubstituted or substituted ammonium cation and m and n are the number zero or 1.

2. A pyrazoline compound according to claim 1, which has the formula

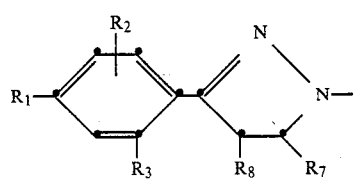

(2)

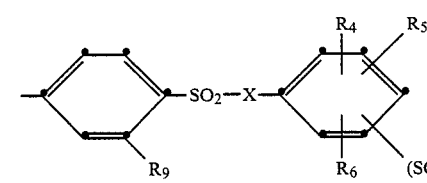

in which
X is 1,4-phenylene,

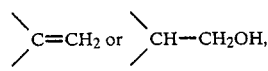

or, if n is 1 or if $R_8$ contains the radical —$SO_3M$, X is also a linear $C_1$-$C_4$alkylenoxy group, oxygen or a direct bond, $R_1$ to $R_3$ are H, Cl or methyl, $R_4$ and $R_5$ are H, Cl, $C_1$-$C_4$alkyl, $C_1$-$C_4$alkoxy or phenoxy or together are the members required to form a tetraline or indane ring, $R_6$ is H or methyl, $R_7$ is H or phenyl, $R_8$ is H, $C_1$-$C_4$alkyl or —$CH_2SO_3M$, $R_9$ is H or Cl, and n and M are as defined under formula 1.

3. A pyrazoline compound according to claim 1, which has the formula

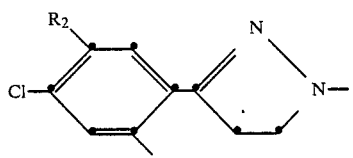

(3)

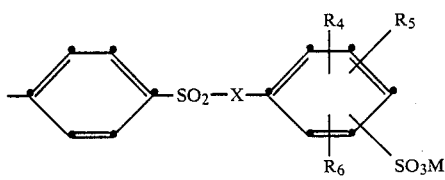

in which
X is the methylene group, a linear $C_1$-$C_4$alkylenoxy group or a direct bond, $R_2$ and $R_3$ are hydrogen, chlorine or methyl, $R_4$ and $R_5$ are hydrogen, chlorine, $C_1$-$C_4$alkyl or methoxy or together are the members required to form a tetraline ring, and $R_6$ and M are as defined in formula 2.

4. A pyrazoline compound according to claim 1, which has the formula

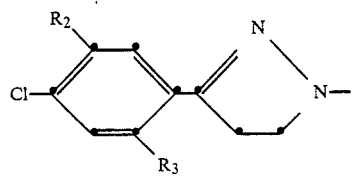

(4)

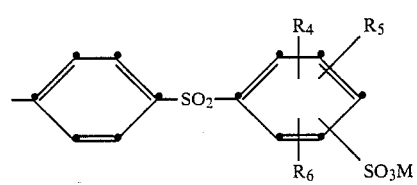

in which
$R_2$ is hydrogen or chlorine, $R_3$ is hydrogen or methyl, $R_4$ is hydrogen or $C_1$-$C_4$alkyl, $R_5$ and $R_6$ are hydrogen or methyl, and M is as defined in formula 2.

5. A method for the fluorescent brightening of fibers or lacquers composed of acetylcellulose, wool and polyamide which comprises treating said fibers or lacquers with a pyrazoline compound of the formula

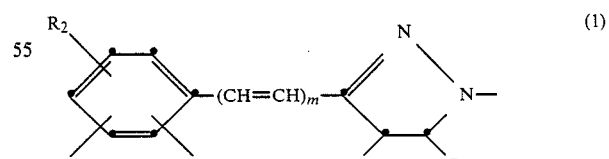

(1)

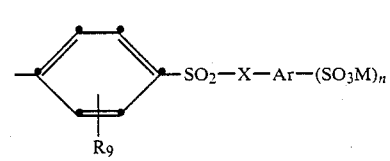

in which

X is 1,4-phenylene,

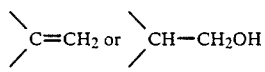

or, if n is 1 or if $R_7$ or $R_8$ contains an $SO_3M$ radical, X is also a methylene or $-CH_2CH(OH)-CH_2O-$ group or an unbranched $C_1-C_4$alkyleneoxy group, a direct bond or oxygen, $R_1$, $R_2$ and $R_3$ independently of one another are hydrogen, chlorine or $C_1-C_4$alkyl, $R_7$ is $C_1-C_4$alkyl, chlorophenyl, hydrogen, phenyl or $-C_6H_4-SO_3M$, $R_8$ is H, $C_1-C_4$alkyl, $-CH_2SO_3M$, carboxyl, $C_2-C_5$carboalkoxy, carbamoyl or carboxymethyl, $R_9$ is H, chlorine or $C_1-C_4$alkyl, Ar is a phenyl radical which is unsubstituted or substituted by a non-chromophore or, if X is a direct bond, Ar is also a naphthalene radical, M is hydrogen or one equivalent of a an alkali metal, an alkaline earth metal or an unsubstituted or substituted ammonium cation and m and n are the number zero or 1.

6. An agent for the fluorescent brightening of fibres and paints composed of acetylcellulose, wool and polyamide, which contains one or more pyrazoline compounds of the formula

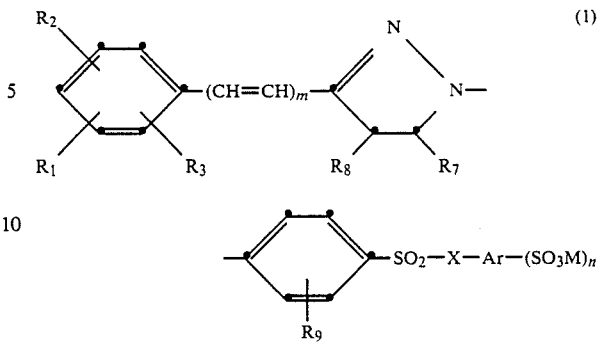 (1)

in which
X is 1,4-phenylene,

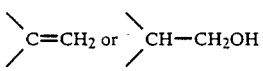

or, if n is 1 or if $R_7$ or $R_8$ contains an $SO_3M$ radical, X is also a methylene or $-CH_2CH(OH)-CH_2O-$ group or an unbranched $C_1-C_4$alkyleneoxy group, a direct bond or oxygen, $R_1$, $R_2$ and $R_3$ independently of one another are hydrogen, chlorine or $C_1-C_4$alkyl, $R_7$ is $C_1-C_4$alkyl, chlorophenyl, hydrogen, phenyl or $-C_6H_4-SO_3M$, $R_8$ is H, $C_1-C_4$alkyl, $-CH_2SO_3M$, carboxyl, $C_2-C_5$carboalkoxy, carbamoyl or carboxymethyl, $R_9$ is H, chlorine or $C_1-C_4$alkyl, Ar is a phenyl radical which is unsubstituted or substituted by a non-chromophore or, if X is a direct bond, Ar is also a naphthalene radical, M is hydrogen or one equivalent of an alkali metal, an alkaline earth metal or an unsubstituted or substituted ammonium cation and m and n are the number zero or 1.

* * * * *